United States Patent [19]

Bennett et al.

[11] E Patent Number: Re. 32,553

[45] Reissued Date of Patent: Dec. 8, 1987

[54] EXHALATION VALVE ASSEMBLY

[76] Inventors: Clifford D. Bennett, 6275 Sacramento, Alta Loma, Calif. 91701; Charles Odenthal, 525 Euclid, Upland, Calif. 91786

[21] Appl. No.: 661,233

[22] Filed: Oct. 15, 1984

Related U.S. Patent Documents

Reissue of:

[64] Patent No.: 4,241,756
Issued: Dec. 30, 1980
Appl. No.: 964,682
Filed: Nov. 29, 1978

[51] Int. Cl.[4] ..... F16K 15/14

[52] U.S. Cl. ..... 137/271; 137/528; 137/859; 137/906; 137/908

[58] Field of Search ..... 137/102, 269, 271, 496, 137/528, 859, 908, 906; 251/61.1; 92/6 R, 6 D; 91/25

[56] References Cited

U.S. PATENT DOCUMENTS

| | | | |
|---|---|---|---|
| 648,593 | 5/1900 | Metzger | 92/6 R |
| 1,007,929 | 11/1911 | Deacon et al. | 210/87 |
| 2,323,839 | 7/1943 | Nixon . | |
| 2,463,865 | 3/1949 | Gilfillan . | |
| 2,638,127 | 5/1953 | Griswold | 137/859 X |
| 2,648,518 | 8/1953 | Curtis . | |
| 2,811,172 | 10/1957 | Frazel | 92/6 R |
| 3,252,471 | 5/1966 | Olson | 92/6 R |
| 3,419,031 | 12/1968 | Hesse et al. | 137/859 X |
| 3,610,236 | 10/1971 | Smilg | 137/835 X |
| 3,633,605 | 1/1972 | Smith | 137/859 X |
| 3,826,255 | 7/1974 | Havstad et al. | 128/200.18 |
| 3,933,171 | 1/1976 | Hay | 137/493.7 |
| 4,022,244 | 5/1977 | Oman | 137/859 X |
| 4,161,947 | 7/1979 | Copson | 137/908 X |

FOREIGN PATENT DOCUMENTS

| | | | |
|---|---|---|---|
| 673007 | 12/1964 | Belgium . | |
| 422407 | 1/1935 | United Kingdom | 137/859 |
| 1007029 | 10/1965 | United Kingdom . | |
| 1014614 | 12/1965 | United Kingdom . | |
| 1260934 | 1/1972 | United Kingdom . | |
| 1264709 | 2/1972 | United Kingdom . | |
| 1462176 | 1/1977 | United Kingdom . | |
| 1553939 | 10/1979 | United Kingdom . | |
| 2015349 | 9/1979 | United Kingdom . | |

*Primary Examiner*—Martin P. Schwadron
*Assistant Examiner*—Stephen M. Hepperle
*Attorney, Agent, or Firm*—Spensley Horn Jubas & Lubitz

[57] ABSTRACT

An exhalation valve assembly for use in a volume ventilator circuit is disclosed. The valve assembly comprises a valve body defining a chamber with a gas inlet conduit and a gas outlet conduit, both in flow communication with the chamber. A diaphragm extends across the chamber and selectively closes off the gas inlet conduit. Upwardly extending strut members are disposed on an inside surface of the valve body and are used to position a removable ring member adjacent the diaphragm. The ring member is configured so as to support a portion of the diaphragm over the chamber.

12 Claims, 4 Drawing Figures

EXHALATION VALVE ASSEMBLY

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to respiratory therapy devices, and more particularly, to the design and construction of an exhalation valve assembly which can be modified for use in various volume ventilator circuits.

2. Prior Art

Volume ventilator circuits utilize an exhalation valve assembly to hold and maintain pressure within the circuit and selectively allowing gases to be exhaled by the patient and to escape therefrom. Such valve assemblies are comprised of a valve body and have a gas inlet conduit, which forms a gas discharge port within the valve body, and a gas outlet conduit. A flexible diaphragm selectively closes off the discharge port during inspiration. When the patient exhales, the diaphragm is pushed away from the port so as to allow the exhaled gases to escape from the valve body through the gas outlet conduit.

The pressure holding capability of a volume ventilator circuit is dependent upon a number of factors including the ratio of the area of the diaphragm which extends across the chamber of the valve (hereinafter referred to as the "effective area") to the area of the gas discharge port. For ease of reference, the ratio of the effective area of the diaphragm to the area of the discharge port is referred to herein as the "valve area ratio."

One of the most widely used volume ventilators in the respiratory therapy field has a limited capability for holding elevated Positive End Expiration Pressure ("P.E.E.P.") when using a circuit with a valve assembly having a valve area ratio usually below 1.5. The valve assembly used in such a circuit is specifically designed to achieve this ratio and cannot be modified so as to be used in another circuit requiring a different ratio.

Another popular volume ventilator works on a somewhat different principal. This machine is not dependent upon the valve area ratio for high P.E.E.P. pressures, but is dependent on the valve area ratio for low patient exhalation effort beyond P.E.E.P. pressures. To achieve the required valve area ratio, the valve assembly is specifically designed and cannot be modified to provide a different valve area ratio for use in a different machine.

Thus, prior art volume ventilators have required the use of specifically designed valve asemblies in order to achieve the desired valve area ratio. Notwithstanding the increased costs of manufacturing one specific valve for one type of machine and yet another valve for another type of machine, the prior art has been unable to provide any interchangeability of such valve assemblies.

In other pressure circuits, the valves are also specifically designed for each circuit. An example of a prior art valve assembly for use in a pneumatic control system is shown in U.S. Pat. No. 3,633,605. This valve assembly employs a flexible diaphragm which selectively closes off one of two inlet ports. When the pressure from gas entering one inlet port is greater than that in the other inlet port, the diaphragm is pushed away from that port with the higher pressure, opening it to gas flow. The other port is occluded, thereby preventing gas flow. This valve assembly is designed such that there is no easy way to change the valve area ratio without constructing a whole new housing and diaphragm each having different dimensions. Because of this fact, such valve assembly cannot easily be used in a different system requiring a different valve area ratio.

Yet another valve assembly is disclosed in U.S. Pat. No. 3,419,031. The valve shown in that patent also suffers from the above identified limitations. More specifically, such valve assembly includes a specifically designed resilient valve element which has dimensions related to the dimensions of the inlet and outlet conduits. As discussed hereinabove, it is not readily apparent how one could alter such assembly so as to use the valve in a different system.

Thus, the prior art valve assemblies suffer from the shortcoming of using a specifically configured valve assembly. This leads to a proliferation of valve assemblies all fundamentally designed to perform the same function. The present invention overcomes these problems by providing a valve assembly which can be easily modified so as to achieve different valve area ratios. In this manner, one valve body can be made for use in different environments. The expense of constructing entirely different valve assemblies for use in different pressure circuits is thereby obviated.

SUMMARY OF THE INVENTION

It is one object of the present invention to provide an exhalation valve assembly with a simple, inexpensive means for changing the area ratio of the valve without entirely reconstructing such valve.

Another object of this invention is to provide an exhalation valve assembly which can be used in different volume ventilator circuits.

In general, the exhalation valve assembly of the present invention is designed for use in gas flow circuitry such as a volume ventilator circuit. The valve assembly includes a valve body having a chamber in flow communication with a gas inlet conduit and a gas outlet conduit. The gas inlet conduit is configured to be coupled to a patient connection such that exhaled gases from the patient are directed through a gas discharge port into a chamber formed in the valve body. The gas outlet conduit directs the exhaled gas out of the chamber.

A diaphragm extends across the chamber formed in the valve body, and is configured to selectively close off the discharge port. The diaphragm is held in position by a removable cap which permits the easy replacement of the diaphragm with diaphragms of different configurations.

Circumferentially disposed around the chamber on the internal wall of the valve body are a plurality of upwardly extending strut members. These strut members are used to support a ring member which supports a portion of the diaphragm from extending across the chamber. This reduces the effective area of the diaphragm. Accordingly, when the ring member is used, the ratio of the effective area of the diaphragm to the area of the discharge port is decreased.

By the use of the valve assembly of the present invention, the valve area ratio can easily be modified so as to meet the needs of the specific circuit in which the assembly is to be used. More specifically, one need merely remove the cap from the assembly, remove the diaphragm and ring member, and insert a different diaphragm or diaphragm/ring combination. The cap is then replaced and the assembly is now ready to be used.

The operation of the valve assembly in any configuration basically is the same. During inspiration, the diaphragm closes off the discharge port thus preventing any gas from traveling through the valve assembly. This action is achieved by the application of positive pressure over the diaphragm as more fully discussed herein. Upon exhalation, the exhaled gas travels through the inlet conduit. The pressure exerted by the gas forces the diaphragm to disengage from the discharge port thereby allowing the exhaled gas to enter the body of the valve where it is directed out of the valve body through the outlet conduit. If a ring member is being used, the pressure needed to disengage the diaphragm from the discharge port is less than if a diaphragm is used without a ring member. This is because the ring member supports a portion of the diaphragm thus reducing its effective area. The valve area ratio (effective area of the diaphragm—area of discharge port) is greater without the ring member than with the ring member. Thus, by using a specific diaphragm and ring combination or omitting the ring member, the valve assembly can be modified so as to meet the specific valve area ratio needs of a given volume ventilator circuit.

The novel features which are believed to be characteristic of the invention, both as to its organization and method of operation, together with further objectives and advantages thereof, will be better understood from the following description considered in connection with the accompanying drawings in which a presently preferred embodiment of the invention is illustrated by way of example. It is to be expressly understood, however, that the drawings are for the purpose of illustration and description only, and are not intended as a definition of the limits of the invention.

DETAILED DESCRIPTION OF THE INVENTION

1. The Device

Figure 1:
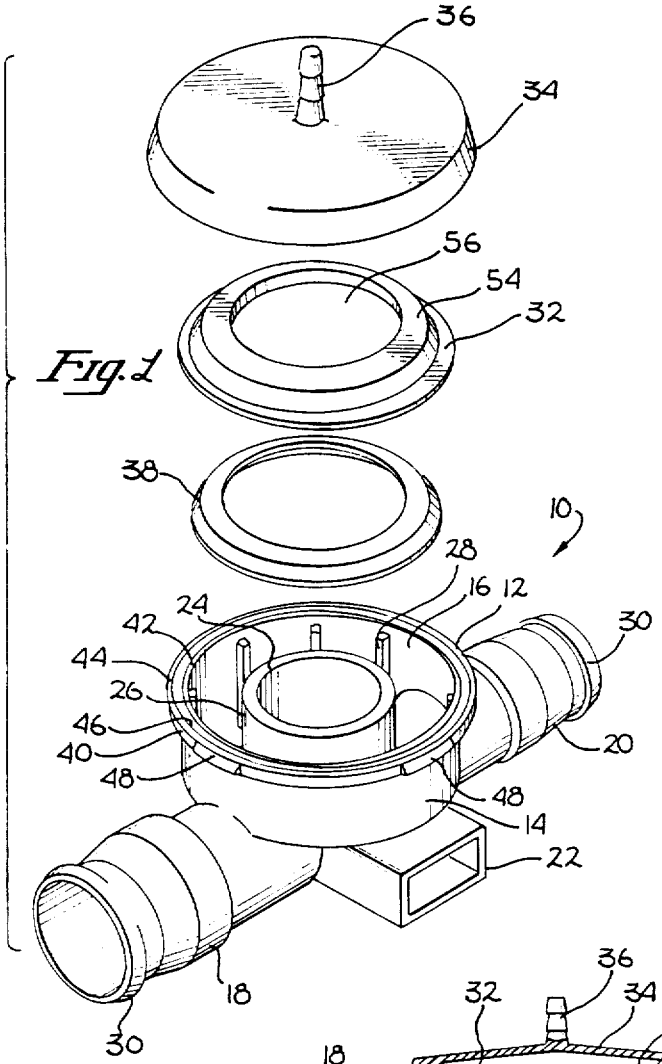
FIG. 1 is an exploded perspective view of the exhalation valve assembly of the present invention.

Referring first to FIG. 1, the valve assembly 10 of the present invention is shown. The valve assembly 10 is comprised of a valve body 12 forming a generally circular housing 14 defining a chamber 16. An inlet conduit 18 and an outlet conduit 20 are in flow communication with chamber 16. Disposed on the inside wall of the valve body 12 are a plurality of upwardly extending support members or struts 28. As is hereinafter discussed, such support members 28 are used to position a ring member inside the housing 14. Also disposed on the valve body 12, adjacent the bottom thereof, is an outwardly extending and generally rectangular mounting support member 22. Such mounting support member 22 enables the valve assembly 10 to be attached to a support structure (not shown) and thereby held in a predetermined position.

One end of the inlet conduit 18 includes a section 26 which extends into the chamber 16 and forms a circular gas discharge port 24. In the preferred embodiment, port 24 is circumferentially disposed in chamber 16. The other end of the inlet conduit 18 as well as the outlet conduit 20 each have specifically configured coupling ends 30 as are well known in the art. Such ends 30 enable the conduits to be readily joined to flexible tubing (not shown) or to other elements in a volume ventilator circuit.

The valve assembly 10 also includes a flexible, circular diaphragm member 32 which is disposed across the chamber 16. A cap or cover 34 snap locks onto the body 12 as hereinafter described and holds the diaphragm 32 across the chamber 16. Centrally located on the cover 34 is a gas inlet port 36 which can be used to direct a gas into the assembly 10. Note, however, that in the preferred embodiment, gas from part 36 does not flow into chamber 36, but only into the area above diaphragm 32. In this manner, the pressure above the diaphragm 32 can be regulated.

Figure 3:
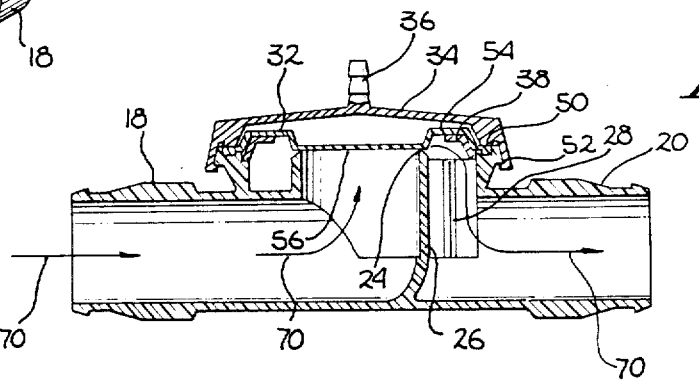
FIG. 3 is a cross-sectional view taken along lines 2—2 of FIG. 1 and showing the internal aspects of the valve assembly using a first diaphragm.

In the first embodiment of the present invention, a circular, plastic ring member 38 is disposed in the valve body 12 and rests on the support members 28. This is illustrated in FIGS. 1 and 3. In the preferred embodiment, ring member 38 is disposed in the body 12 adjacent the periphery of chamber 16 and circumferentially surrounds the gas discharge port 24. It is to be understood, however, that other means for supporting ring member 38 in the valve body 12 are within the scope of this invention. Once the ring member 38 is in position, the diaphragm 32 is then placed over it. The diaphragm 32 includes an upwardly extending section 54 configured to arch over the ring member 38, and a generally circular section 56 which is used to selectively close off the gas discharge port 24. The diaphragm 32 rests on a grooved area 46 formed by an inner wall 42 and an outer wall 44 on the valve body 12. When the cover 34 is disposed over the diaphragm 32, as is more clearly shown in FIG. 3, it snap locks over lip 40. More specifically, a rim 52 on cover 34 snap locks over the lip 40 and is held in position by outwardly extending tab members 48 formed on the periphery of the lip 40. A circular ledge 50 formed on an inside surface of the cover 34 presses the diaphragm 32 into the groove 46. This holds the diaphragm 32 in position. It is to be understood, however, that other means for holding the diaphragm 32 in position are within the scope of the invention.

Again referring to FIG. 3, one can see that ring member 38 supports a portion of the diaphragm 32 thereby occluding such portion of the diaphragm 32 from extending across the chamber 16. Thus, the effective area of the diaphragm 32 over the chamber 16 is decreased thereby decreasing the valve area ratio. In turn, less pressure is required to raise the diaphragm 32 off of the gas discharge port 24.

Figure 2:
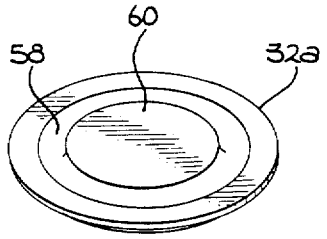
FIG. 2 is a perspective view of one of the diaphragms used with the valve assembly of the present invention.
Figure 4:
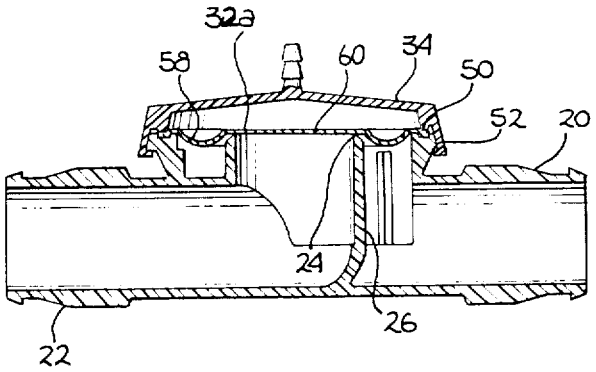
FIG. 4 is a cross-sectional view taken along lines 2—2 of FIG. 1 and showing the internal aspects of the valve assembly using a second diaphragm.

A second embodiment of the present invention will now be discussed with reference to FIGS. 2 and 4. In the second embodiment, the ring member 38 has been removed and a circular diaphragm 32A of slightly different configuration than diaphragm 32 is inserted into the valve body 12. In the second embodiment, with the ring member 38 removed, the diaphragm 32A is configured so as to have a generally downwardly extending section 58 and a circular section 60 which is disposed above and adjacent to the discharge port 24. Section 60 acts to close off discharge port 24 in the same manner as section 56 of the first diaphragm 32. All the other elements of the valve body 12 in the second embodiment remain the same.

2. Operation of the Valve Assembly

The operation of the valve assembly 10 of the present invention will now be discussed. In operating the valve assembly 10 in one manner, a patient connection hose (not shown) is joined to the gas inlet conduit 18 and secured thereto by means of the coupling end 30. Likewise, an outlet hose (not shown) is joined to the gas outlet conduit 20 and secured thereto by coupling end 30. During inspiration, it is necessary to maintain a positive pressure above diaphragm 32. Therefore, a gas supply tube is joined to the gas inlet port 36 on the cover 34 such that a gas is directed into the assembly 10 above the diaphragm 32 or 32A. This enables a positive pressure to be created above the diaphragm. During exhalation, it is sometimes desirable to maintain a positive pressure above the diaphragm, thus forcing the patient to exert an elevated pressure in order to exhale past the diaphragm. The elevated pressure exerted is determined by the air pressure applied above the diaphragm and the valve area ratio. It is to be understood, however, that in other applications, it may be desirable not to maintain such positive pressure. In that case, no pressure would be maintained above diaphragm during exhalation.

Referring now to FIG. 3 one can see arrows 70 which generally indicate the flow of gas for example, exhaled gas from a patient, as it would be directed through the assembly 10 in the first embodiment of the present invention. More specifically, when the patient exhales with sufficient pressure, the pressure above the diaphragm 38 (positive pressure supplied by a gas source or atmospheric) is overcome. This causes the diaphragm 32 to disengage port 24. The exhaled gas then flows through the inlet conduit 18, through gas discharge port 24 and into the chamber 16. The exhaled gas would flow out of the chamber 16 through the outlet conduit 20. During inspiration a positive pressure is created in the assembly 10 above diaphragm 32 causing section 56 of the diaphragm 32 to engage port 24. This prevents gas from escaping from the patient circuit through the valve assembly 10. Air or other gas to the patient comes from the ventilator, connected to patient circuit upstream from valve assembly 10.

As discussed hereinabove, prior art ventilator circuits were designed such that specific amounts of pressure were required in order to cause the diaphragm 32 to disengage the discharge port 24 thereby permitting escape of the exhaled gas. The present invention enables this to take place, and further enables such pressure to be regulated by the use of a specifically designed ring member and diaphragm. Ring member 38 extends towards the center of the chamber 16 and in one embodiment supports a portion of the diaphragm 32. Because ring 38 acts as a support for a section of the diaphragm 32, the amount of force necessary to disengage the diaphragm 32 from the discharge port 24 is decreased. If one desired to increase the force necessary to disengage the diaphragm 32 from the port 24, the ring member 38 could be removed and/or a different diaphragm or ring used. For example, in the second embodiment the pressure necessary to disengage the diaphragm from the port 24 is increased by interchanging diaphragm 32 with diaphragm 32A and by removing the ring member 38 from the assembly 10. Diaphragm 32A is not supported by any ring member and therefore a larger effective area is presented. This larger effective area necessitates the use of more pressure in order to disengage the diaphragm 32A from the discharge port 24. It has been found that by using diaphragm 32 and ring member 38, the valve area ratio is approximately 1:1 although modification in the ring 38 or diaphragm 32 can lead to a valve area ratio between 1:1 and 2:1. Using diaphragm 32A without any ring member yields a valve area ratio of approximately 2:1. Other valve area ratios greater than 2:1 are also within the scope of the present invention.

Thus, the present invention provides a solution whereby one valve body may be produced and used in a variety of pressure circuits. If one desires to change the effective area ratio of the valve assembly 10, the cover 34 can easily be removed from the body 10 by merely snapping the cover 34 off the lip 40 and by removing the diaphragm 32 as well as the ring member 38. Another diaphragm, for example, diaphragm 32A, can then be inserted and the cover 34 again snapped on to the valve body 12. The assembly 10 is now ready for use in a different circuit requiring a different valve area ratio.

A wide variety of materials, shapes and other configurations can be used in this invention. It should therefore be understood that changes can be made without departing from the overall scope or spirit. For example, in the preferred embodiment all of the parts of the present invention are made out of plastic material such as nylon, PVC, acrylic resins and the like. Of course, other materials such as reinforced plastics or even metals are within the scope of the present invention. Further, the shape of the diaphragm and the ring member can be modified so as to achieve various valve area ratios. This invention, therfore, is not to be limited to the specific embodiments discussed and illustrated herein.

What is claimed:

1. A valve assembly for use in a volume ventilator, comprising:

(a) a valve body in part defining a pressure chamber, *said valve body having an annular diaphragm seat*;

(b) a gas inlet conduit joined to and in flow communication with said pressure chamber for directing a gas into said pressure chamber, said gas inlet conduit forming a discharge port in said pressure chamber;

(c) a gas outlet conduit joined to and in flow communication with said pressure chamber for directing gas out of said pressure chamber;

(d) diaphragm means removably disposed in and extending across said valve body adjacent said discharge port for selectively closing off said discharge port, said diaphragm means defining the remainder of said pressure chamber;

(e) a removably disposed ring member extending into said pressure chamber from a position adjacent the periphery thereof;

(f) a plurality of positioning members disposed on said body for positioning said ring member in said pressure chamber such that said ring member supports a predetermined portion of said diaphragm means; and (g) a cover having a gas inlet joined to said valve body and extending across said diaphragm means on the opposite side thereof from said pressure chamber;

*(h) said cover having an annular lip and said diaphragm means is sealed at its periphery between said annular lip and said diaphragm seat; and*

*(i) the removably disposed ring member interfitting with a portion of the diaphragm means and the valve body such that by removing said ring member a valve assembly having a substantially different valve area ratio may be achieved, permitting the valve assembly to be used in different volume ventilator circuits.*

2. A valve according to claim 1 wherein said chamber is cylindrical and said discharge port is centrally disposed in said chamber.

3. A valve according to claim 1 wherein said positioning means comprises a plurality of strut members.

4. A valve according to claim 1 wherein the ratio of the area of said diaphragm means extending across said pressure chamber to the area of said discharge port is approximately 2:1.

5. A valve according to claim 1 wherein said ring member supports a portion of said diaphragm means such that the ratio of the unsupported area of said diaphragm means extending across said pressure chamber to the area of said discharge port is approximately from 1:1 to 2:1.

6. A valve according to claim 1 wherein said positioning members comprise a plurality of strut members located on said valve body, and said ring member is removably disposed on said strut members.

7. A valve according to claim 1 wherein said diaphragm means includes a section which is positioned between said cover and said ring member.

*8. A valve assembly for use in a volume ventilator, comprising:*

*(a) a valve body in part defining a pressure chamber, said valve body having an annular diaphragm seat;*

*(b) a gas inlet conduit joined to and in flow communication with said pressure chamber for directing a gas into said pressure chamber, said gas inlet conduit forming a discharge port in said pressure chamber;*

*(c) a gas outlet conduit joined to and in flow communication with said pressure chamber for directing gas out of said pressure chamber;*

*(d) diaphragm means removably disposed in and extending across said valve body adjacent said discharge port for selectively closing off said discharge port, said diaphragm means defining the remainder of said pressure chamber;*

*(e) a removably disposed ring member extending into said pressure chamber from a position adjacent the periphery thereof;*

*(f) a plurality of positioning members disposed on said body for positioning said ring member in said pressure chamber such that said ring member in said pressure chamber such that said ring member supports a predetermined portion of said diaphragm means;*

*(g) said ring member being of substantial area, thus significantly decreasing the effective area of the diaphragm means with respect to the area of the discharge port, and in turn decreasing the valve area ratio; and*

*(h) a cover having a gas inlet joined to said valve body and extending across said diaphragm means on the opposite side thereof from said pressure chamber, said cover having an annular lip and said diaphragm means is sealed at its periphery between said annular lip and said diaphragm seat; and*

*(i) by removing said ring member a valve assembly having a substantially different valve area ratio may be achieved.*

*9. A valve assembly according to claim 8 wherein, when the ring member is removed, the effective area of the diaphragm means with respect to the discharge port is substantially changed, significantly increasing the valve area ratio.*

*10. A valve assembly according to claim 8 wherein said ring member includes a portion that extends into said pressure chamber and mates with a section of the diaphragm means, said ring member thereby substantially changing the amount of force required to disengage the diaphragm from said discharge port.*

*11. A valve assembly according to claim 8 wherein the plane defined by the inner portion of the ring member is laterally offset from the plane defined by the rim of the ring member, said laterally offset inner portion of the ring member supporting said predetermined portion of said diaphragm means thereby occluding said portion of the diaphragm from extending across said discharge port.*

*12. A valve assembly according to claim 11 wherein said ring member is positioned between said diaphragm means and said discharge port, and wherein said diaphragm means includes a section extending away from said discharge port and configured to arch over said ring member.*

* * * * *